(12) United States Patent
Yamamoto

(10) Patent No.: US 8,984,943 B2
(45) Date of Patent: Mar. 24, 2015

(54) INSPECTION APPARATUS AND INSPECTION METHOD FOR LITHIUM ION SECONDARY BATTERY, AND SECONDARY BATTERY MODULE

(75) Inventor: Tsunenori Yamamoto, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 292 days.

(21) Appl. No.: 13/488,884

(22) Filed: Jun. 5, 2012

(65) Prior Publication Data

US 2012/0304771 A1 Dec. 6, 2012

(30) Foreign Application Priority Data

Jun. 6, 2011 (JP) ................................. 2011-125931

(51) Int. Cl.
*G01R 31/36* (2006.01)
*G01N 29/14* (2006.01)
(52) U.S. Cl.
CPC ........ *G01N 29/14* (2013.01); *G01N 2291/2697* (2013.01)
USPC .............................................. 73/587; 73/646
(58) Field of Classification Search
USPC ...................... 73/579, 584, 58, 647
See application file for complete search history.

(56) References Cited

U.S. PATENT DOCUMENTS

| 4,388,583 | A | * | 6/1983 | Krueger ......................... 320/147 |
| 6,144,188 | A | * | 11/2000 | Okada et al. ................... 320/141 |
| 2013/0091950 | A1 | * | 4/2013 | Bernard .......................... 73/587 |

FOREIGN PATENT DOCUMENTS

| JP | 7-6795 A | 1/1995 |
| JP | 7-85892 A | 3/1995 |
| JP | 2003-308885 A | 10/2003 |
| JP | 2009-170348 A | 7/2009 |
| JP | 2009-176511 A | 8/2009 |
| JP | 2010-40318 A | 2/2010 |
| JP | 2010-54428 A | 3/2010 |
| JP | 2010-80223 A | 4/2010 |
| JP | 2010-261807 A | 11/2010 |

OTHER PUBLICATIONS

English Translation of Yasuda et al. (JP 2010-080223).*

* cited by examiner

*Primary Examiner* — Peter Macchiarolo
*Assistant Examiner* — Alexander Mercado
(74) *Attorney, Agent, or Firm* — Crowell & Moring LLP

(57) ABSTRACT

The present invention provides an inspection method for a lithium ion secondary battery in which an electrolyte and an electrode group are disposed in one container, the electrode group including a positive electrode, a negative electrode, and a separator, wherein a sensor for detecting acoustic emission is attached to the outside of the container and acoustic emission generated in the battery container is detected upon provision of charge or discharge current and stopping of provision thereof between the positive electrode and the negative electrode. Specifically, the amplitude intensity of the acoustic emission is measured that is generated upon provision of charge-discharge currents having different values, linear approximation is conducted for the charge-discharge current value and the amplitude intensity of the acoustic emission, and the number of times of charge-discharge cycles that has been provided so far to the battery is estimated.

8 Claims, 4 Drawing Sheets

INSPECTION APPARATUS AND INSPECTION METHOD FOR LITHIUM ION SECONDARY BATTERY, AND SECONDARY BATTERY MODULE

BACKGROUND OF THE INVENTION

1. Field of the Invention

The present invention relates to an inspection method, etc. for degradation of a lithium ion secondary battery.

2. Description of the Related Art

Automobiles or railway vehicles have secondary batteries mounted thereon such as a lead acid battery, a nickel metal hydride battery, and a lithium ion battery, charge an electric power obtained by a regeneration brake to the secondary batteries, and utilize the electric power obtained upon acceleration, etc. Such secondary batteries are used for hybrid cars in which improved fuel consumption is achieved, and electric cars driven by electric energy stored in the secondary batteries. Further, it is requested in the field of wind power generation or solar power generation that leveling in a load by using a secondary battery system be attained upon connections with a power transmission system so that renewable energy subject to fluctuations may be converted into electricity.

It is very important to know the state of degradation of secondary batteries being used in the secondary battery systems for use in vehicles such as hybrid cars and electric cars or power storage. Further, also when a secondary battery that has been degraded to some extent is diverted to other uses, it is necessary to exactly know how much the secondary battery in question has been degraded.

For example, a method of detecting the state of degradation of a secondary battery is described in JP-2003-308885-A. JP-2003-308885-A involves measuring, at about 1 C rate and at lower than 0.1 C rate, a voltage change profile just before charging or discharging is completed, and comparing the same with each other before and after degradation, thereby determining the degree of degradation of a positive electrode and a negative electrode constituting the battery.

To improve the accuracy in detection of the degradation of a secondary battery, JP-2010-54428-A discloses that means is provided for measuring the temperature of a secondary battery to be subjected to a charge-discharge test and temperature is measured in addition to voltage and current values based on charge-discharge current, thereby improving the accuracy in detection of degradation.

In JP-2010-261807-A, direct current resistance is estimated based on each of the fluctuating components of current and voltage to examine the state of degradation of a battery in use, thereby judging the state of degradation.

Further, JP-2010-40318-A discloses a method in which a plurality of acoustic emission sensors are attached to a battery to investigate the internal state of the battery, thereby detecting where in the inside of the battery the acoustic emission is generated. JP-2009-170348-A and JP-2009-176511-A disclose examples of use of acoustic emission as a method of examining the characteristics of the secondary battery.

SUMMARY OF THE INVENTION

However, detailed inspection for the internal state of the battery by JP-2003-308885-A requires a charge-discharge test at lower than 0.1 C rate in addition to charging and discharging at about 1 C rate, so that the inspection time is extremely long. Further, temperature detection of the battery described in JP-2010-54428-A is liable to depend on the external circumstance and the available information is restricted to the direct current resistance functioning as the generation source of Joule heat. Such information is somewhat insufficient to know the internal state of the battery.

Further, while the detection method described in JP-2010-261807-A is an effective inspection method in a state of actual use, the detectable information is only direct current resistance that is not reliable in accuracy and thus is also insufficient. JP-2010-40318-A is a method of detecting portions where the acoustic emission is generated but this is not a method of directly inspecting the extent of degradation for the internal state.

Further, the method of using the acoustic emission in JP-2009-170348-A and JP-2009-176511-A are methods of obtaining initial characteristics of a secondary battery.

The present invention intends to address problems and subjects as described above. The present invention intends to provide a method of specifically inspecting the internal state of a lithium ion secondary battery, that is, an inspection method and an inspection apparatus capable of inspecting the internal state in a short time and at a higher accuracy by using signals other than electric signals such as current and voltage by a charge-discharge test.

The present invention provides an inspection method for a lithium ion secondary battery in which an electrolyte and an electrode group are disposed in one container, the electrode group including a positive electrode, an negative electrode, and a separator, wherein a sensor for detecting acoustic emission (supersonic waves) is attached firmly to the outside of the container and acoustic emission generated in the battery container is detected upon provision of charge or discharge current and stopping of provision thereof between the positive electrode and the negative electrode.

In particular, the present invention has a feature of detecting the amplitude intensity of the acoustic emission generated upon provision of a plurality of charge-discharge currents of different values and stopping the provision thereof to the battery.

According to the invention, internal state of the battery can be inspected in a short time and at a higher accuracy by detecting acoustic emission in addition to electric signals such as current and voltage based on a charge-discharge test and digitizing the intensity change of the acoustic emission.

BRIEF DESCRIPTION OF THE DRAWINGS

Other objects and advantages of the invention will become apparent from the following description of embodiments with reference to the accompanying drawings in which.

DESCRIPTION OF THE PREFERRED EMBODIMENTS

The present invention will be described for preferred embodiments of the invention with reference to the drawings.

Embodiment 1

Figure 1:
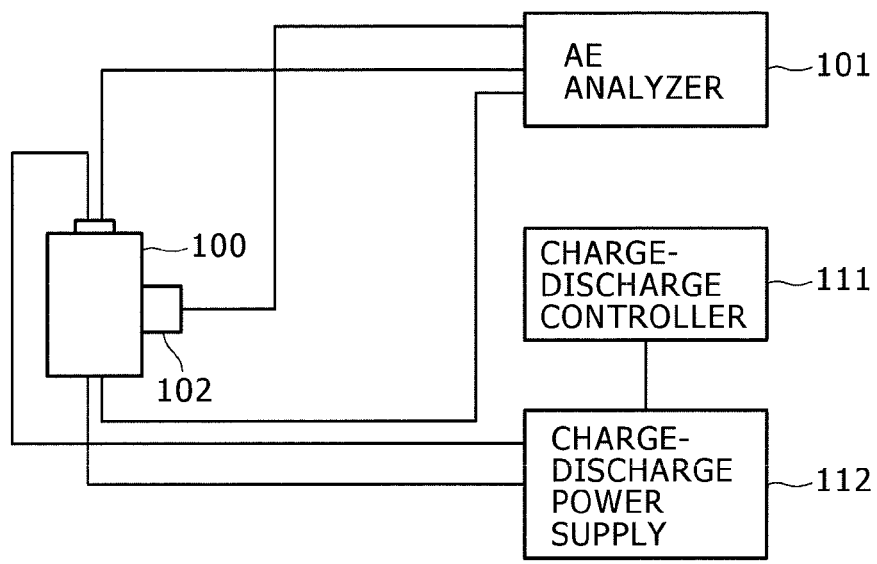
FIG. 1 is a block diagram of an inspection apparatus for a lithium ion secondary battery in an Embodiment 1.

FIG. 1 shows a block diagram of an inspection apparatus for a lithium ion secondary battery in this embodiment. An acoustic emission sensor (hereinafter referred to as an AE sensor 102) is attached firmly to a lithium ion secondary battery 100 as a target of measurement. An AE analyzer 101 takes the output from the sensor therein. Further, a charge-discharge controller 111 provides a charge current or discharge current by way of a charge-discharge power supply 112 to the lithium ion secondary battery 100 and stops the provision of the charge current or discharge current.

The AE analyzer 101 receives the potential difference between the positive electrode and the negative electrode of the lithium ion secondary battery 100. The AE analyzer 101 takes therein the timing for provision of the charge-discharge current from the charge-discharge power supply 112 and stopping the provision thereof.

Figure 2:
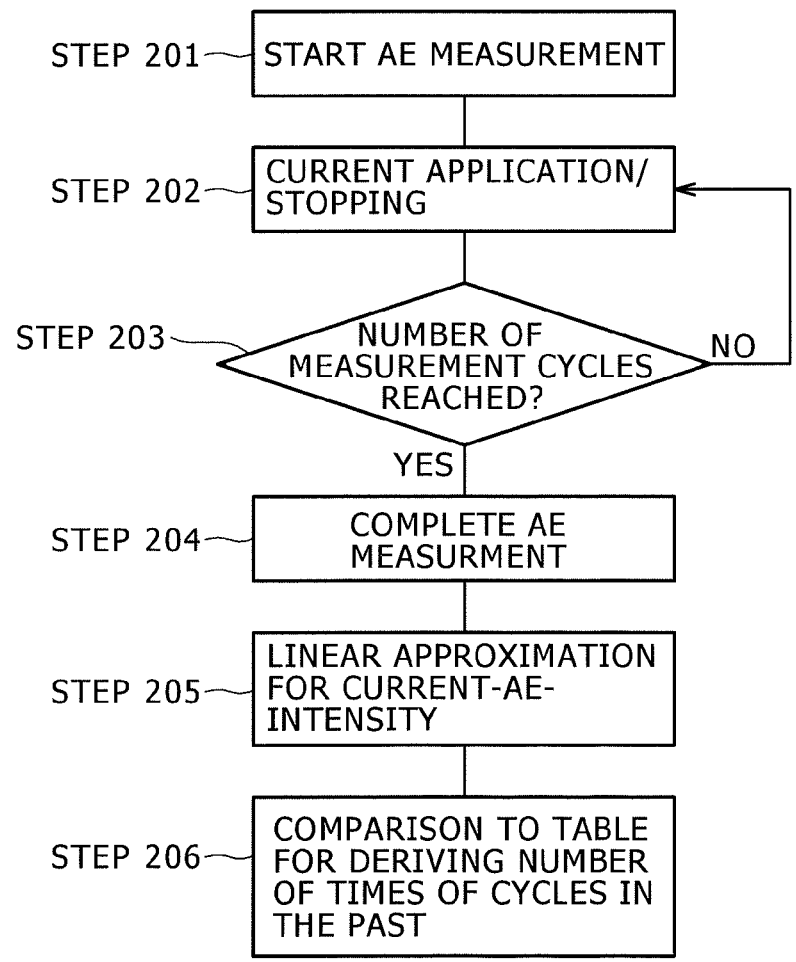
FIG. 2 is a flow chart of an inspection method for the lithium ion secondary battery in the Embodiment 1.
Figure 3:
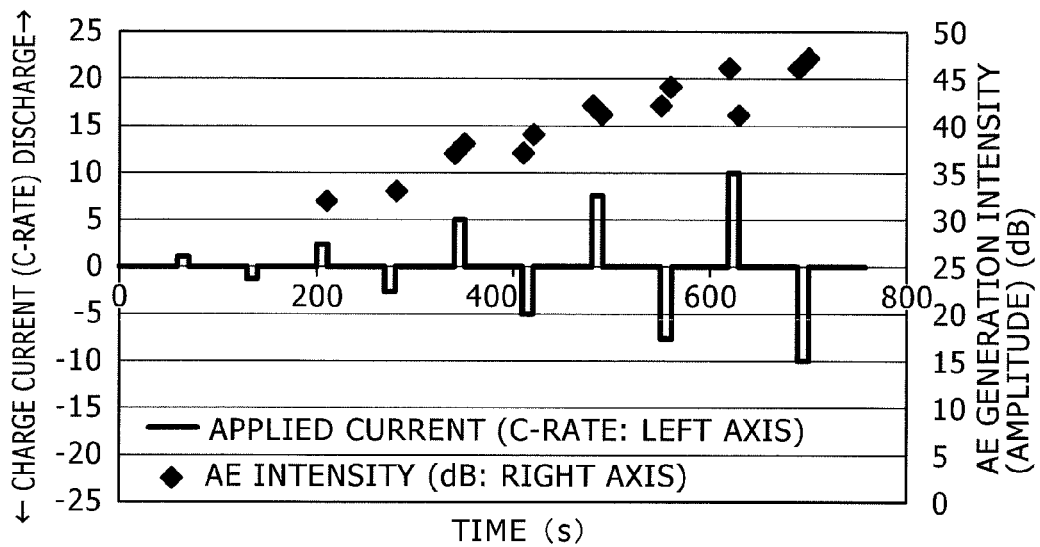
FIG. 3 shows an example of measurement of AE event in the inspection method for the lithium ion secondary battery in the Embodiment 1.

FIG. 2 shows a flow chart of inspection in this embodiment. First, intake of the AE event from the AE sensor 102 is started in the AE analyzer 101 (step 201). Then, the charge-discharge controller 111 is used to start and stop charging or discharging from the charge-discharge power supply 112 to the lithium ion secondary battery 100 as a target of measurement (step 202). Charging-stopping or discharging-stopping is repeated several times while the current value is changed and the intensity of the AE event generated upon current provision or stopping of current provision is recorded (step 203). After charging-stopping or discharging-stopping is repeated until a predetermined current value is reached, the charging or discharging is stopped and the AE measurement is completed (step 204). FIG. 3 shows an example of measurement made up to the step 203.

FIG. 3 shows a measurement cycle of discharging-stopping-charging-stopping measured at five levels of current values respectively. It is defined that the charge or discharge time is 10 seconds, the stopping time is 30 seconds, and the discharge and charge current values are 1 C, 2.5 C, 5 C, 7.5 C, and 10 C along the time axis. 1 C means a current value necessary for charging or discharging, in one hour, a prescribed capacity of the lithium ion secondary battery 100 as a target of measurement.

According to FIG. 3, it can be seen that the AE event is not generated upon provision/stopping of current at a charge-discharge current of 1 C. It can be seen that the AE event is generated at 2.5 C, the AE event is generated both upon provision and stopping of current at higher current, and the AE generation intensity (amplitude value) is also increased along with increase in the current value.

The inspection method will be described further with reference to the flow chart of FIG. 2. After the measurement of the AE event is completed, linear approximation is conducted for the AE intensity and the current value to determine the values for the slope and the intercept (step 205). Then, by comparing the values of the slope and the intercept with a relation of the number of the tested cycles and the slope value and the intercept value which were measured previously, the number of cycles that has been provided so far to the battery until the inspection can be determined.

Figure 4:
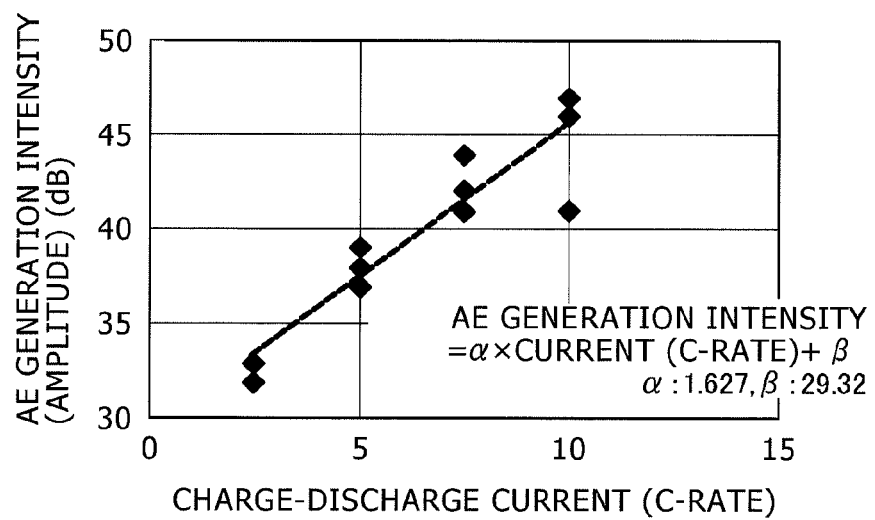
FIG. 4 shows an example of linear approximation of an AE intensity in the inspection method for the lithium ion secondary battery in the Embodiment 1.

FIG. 4 shows an example of the linear approximation for the measurements of the AE event and the current value shown in FIG. 3. The AE generation intensity is represented by the formula: ($\alpha \times$current (C rate)$+\beta$). In this measurement example, the slope value $\alpha$ was 1.627 and the intercept value $\beta$ was 29.32.

Figure 5:
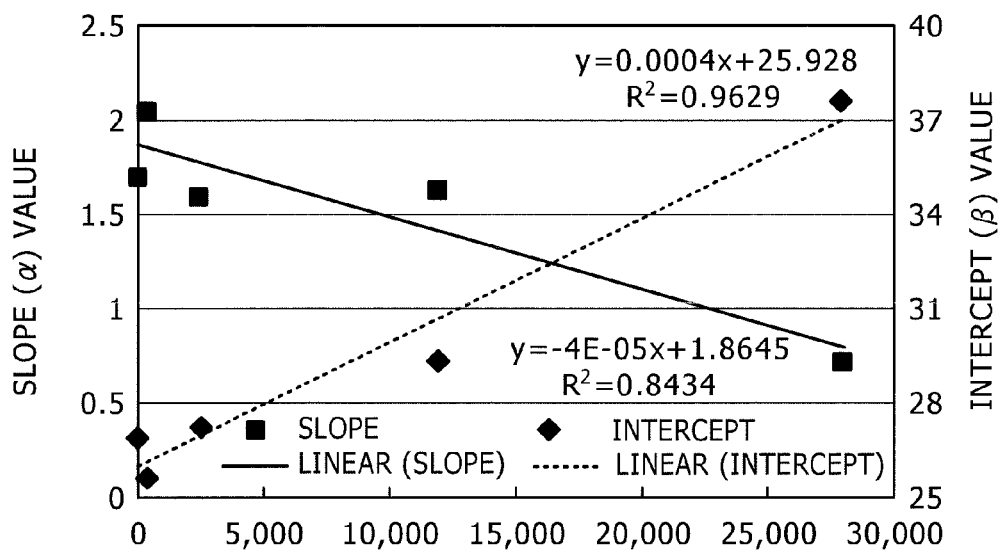
FIG. 5 is a graph showing a relation of slope and intercept values of the AE intensity to the number of cycles in the past in the inspection method for the lithium ion secondary battery in the Embodiment 1.

FIG. 5 shows a relation between the slope value and the intercept value of the lithium ion secondary battery 100 measured for the AE event and the number of cycles tested so far to the lithium ion secondary battery 100. The slope and the intercept of the AE intensity show a linear relation with the number of cycles that has been tested so far to the lithium ion secondary battery 100, and how many the charge-discharge cycles are repeated so far to the lithium ion secondary battery 100 can be judged by measuring the slope value and the intercept value of the AE intensity.

As described above, in the present invention, the AE sensor 102 is attached to the lithium ion secondary battery 100 as a target of measurement. With this, the intensity of the AE event is measured that is generated upon provision/stopping of different charge-discharge current, and the slope and the intercept of the AE intensity to the current value are determined. Thus it is possible to conveniently judge how many charge-discharge cycles have been provided so far to the lithium ion secondary battery 100.

The information obtained through the steps as described above is not one available by merely subjecting the battery as the target of measurement to the charge-discharge test and determining the capacity ratio and the rate of resistance increase.

For example, the lithium ion secondary battery 100 is degraded while it is merely stored at a high temperature (for example 50 to 60° C.) even without charging-discharging. Values of the capacity ratio and the rate of resistance increase after degradation at high temperature storage is not so different in feature from values of the capacity ratio and the rate of resistance increase of the battery degraded through charge-discharge cycles at a room temperature. Therefore the cause of degradation cannot be discriminated if only the capacity ratio and the rate of resistance increase are used as the index for the degradation.

However, since, in the inspection method and the inspection apparatus according to this embodiment, it can be judged how many charge-discharge cycles has been provided before the inspection of the lithium ion secondary battery 100, the state of degradation of the lithium ion secondary battery 100 can be estimated by combining the judgment results with the capacity ratio and the rate of resistance increase.

As described above, according to the invention, the internal state of the battery can be inspected in a short time and at a higher accuracy by detecting the acoustic emission in addition to electric signals such as of current and voltage based on the charge-discharge test and digitizing a change in the intensity of the acoustic emission.

In FIG. 3, while the AE event is generated upon both of provision of current and stopping of current provision at a charge or discharge current of 5 C, 7.5 C, and 10 C, the result of measurement only upon current provision, or the result of measurement only upon stopping of current provision may also be used instead of the result of measurement upon both current provision and stopping of current provision.

Embodiment 2

This embodiment is identical with the Embodiment 1 except for the following points.

Figure 6:
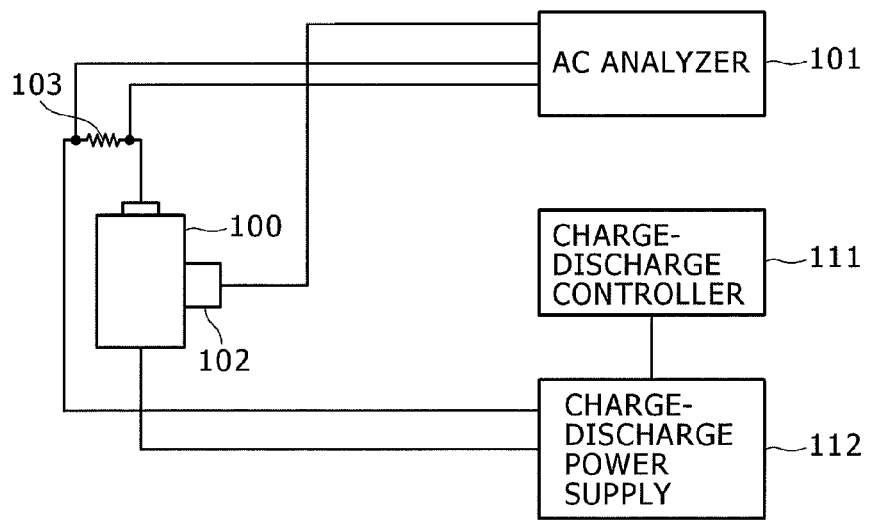
FIG. 6 is a block diagram of an inspection apparatus for a lithium ion secondary battery according to an Embodiment 2.

FIG. 6 shows a block diagram of an inspection apparatus for a lithium ion secondary battery 100 in this embodiment. In this embodiment, the AE analyzer 101 does not receive a voltage between positive and negative electrodes of the lithium ion secondary battery 100 as the target of measurement but receives a voltage across opposite ends of a shunt resistance 103 so that the value of currents charged and discharged to and from the lithium ion secondary battery 100 can be read. With such a configuration, the AE intensity data measured by the AE analyzer 101 can be subjected to the linear approximation with respect to the current value as it is. Thus the calculation is performed with ease even when another lithium ion secondary battery 100 as the target of measurement is tested and thus the current value is changed.

The flow chart of inspection is identical with that of the Embodiment 1. Also in this embodiment, the AE sensor 102 is attached to the lithium ion secondary battery 100 as a target of measurement. With this, the intensity of the AE event is measured that is generated upon provision/stopping of different charge-discharge current, and the slope and the intercept of the AE intensity to the current value are determined. Thus it is possible to conveniently judge how many charge-discharge cycles have been provided so far to the lithium ion secondary battery 100.

From the above, the internal state of the battery can be inspected in a short time and at a higher accuracy by detecting the acoustic emission in addition to the electric signals such as current and voltage based on the charge-discharge test and digitizing a change in the intensity of the acoustic emission also in this embodiment.

Embodiment 3

This embodiment is identical with the Embodiment 1 except for the following points.

Figure 7:
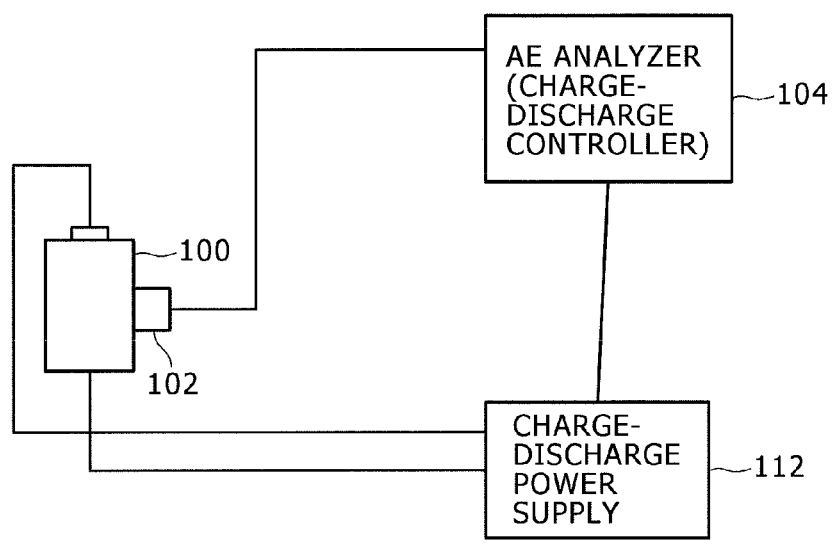
FIG. 7 is a block diagram of an inspection apparatus for a lithium ion secondary battery according to an Embodiment 3.

FIG. 7 shows a block diagram of an inspection apparatus for a lithium ion secondary battery 100 in this embodiment. In this embodiment, an AE analyzer 104 that also serves as a charge-discharge controller is used instead of the AE analyzer 101. By using the charge-discharge controller and the AE analyzer in common, the AE analyzer 104 can know all of the timings for provision/stopping of provision of the charge-discharge current and the value of the provided current. Thus it is no longer necessary to measure the current and voltage provided to the lithium ion secondary battery 100 as the target of measurement, thereby allowing the apparatus to be configured in a very simple manner.

Even if such a configuration is adopted, the inspection flow chart is identical with that of the Embodiment 1 and all of the factors can be inspected by one controller. This permits inspection to be performed extremely conveniently.

Also in this embodiment, the AE sensor 102 is attached to the lithium ion secondary battery 100 as a target of measurement. With this, the intensity of the AE event is measured that is generated upon provision/stopping of different charge-discharge current, and the slope and the intercept of the AE intensity to the current value are determined. Thus it is possible to conveniently judge how many charge-discharge cycles have been provided so far to the lithium ion secondary battery 100.

From the above, the internal state of the battery can be inspected in a short time and at a higher accuracy by detecting the acoustic emission in addition to the electric signals such as current and voltage based on the charge-discharge test and digitizing a change in the intensity of the acoustic emission also in this embodiment.

Embodiment 4

Figure 8:
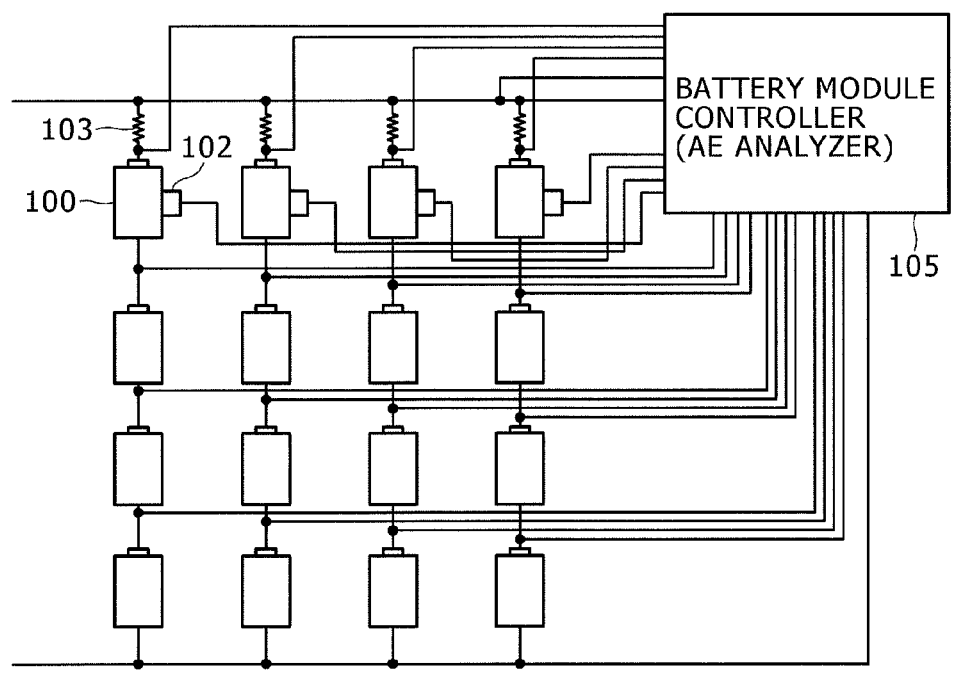
FIG. 8 is a block diagram of an lithium ion secondary battery module in an Embodiment 4.

FIG. 8 shows a block diagram of a lithium ion secondary battery module in this embodiment. This embodiment provides a lithium ion secondary battery module in which lithium ion secondary batteries are arranged in 4×4 serial and parallel connection of cells. One of the lithium ion secondary batteries arranged in each of four columns is used as the lithium ion secondary battery 100 as the target of measurement and an AE sensor 102 is attached firmly to the later lithium ion secondary battery 100. The AE sensor 102 has an output connected to a battery module controller 105 that also serves as an AE analyzer. A current flowing through each of the serial columns is converted into a voltage by a shunt resistance 103 disposed in each of the columns, with the voltage being inputted to the battery module controller 105 that also serves as the AE analyzer. Further, the battery module controller 105 also monitors the voltage of each of the lithium ion secondary batteries.

By adopting the configuration as described above, the secondary battery module according to this embodiment allows the battery module controller 105 to analyze the AE event generated upon starting and stopping of charging and discharging from the outside. Since how many charge-discharge cycles have been provided so far to each of the lithium ion secondary batteries 100 as the target of measurement can be judged by measuring charge and discharge current upon charging and discharging from the outside and the generated AE intensity, it is no longer necessary for the battery module controller 105 or a higher-level device thereof to record the log of the number of charge-discharge cycles. Further, the internal state of the battery can be known at a higher accuracy as compared with the case in which the state of degradation is known only by the current and the voltage.

While, in this embodiment, the batteries are arranged in 4×4 serial-parallel connection and one cell in each of serial columns is used as a battery for AE measurement, the number of batteries in the serial and parallel connection may be different. If all of the batteries are subjected to AE measurement, the state of degradation of the battery module can be known more specifically.

As described above, the present invention can provide a battery module in which the internal state of the battery can be known at a higher accuracy by detecting the acoustic emission in addition to electric signals such as current and voltage based on charging and discharging from the outside and digitizing a change in the intensity of the acoustic emission.

FIG. 1

| | |
|---|---|
| 101 | AE analyzer |
| 111 | Charge-discharge controller |
| 112 | Charge-discharge power supply |

FIG. 2

| | |
|---|---|
| Step 201 | Start AE measurement |
| Step 202 | Current provision/stopping |
| Step 203 | Number of measurement cycles reached? |
| Step 204 | Complete AE measurement |
| Step 205 | Linear approximation for current - AE intensity |
| Step 206 | Comparison to table for deriving number of times of cycles in the past |

FIG. 3
Charge Current (C Rate) Discharge

AE Generation Intensity (Amplitude) (dB)
— Provided current (C-rate: left axis)
♦ AE intensity (dB: right axis)
Time(s)
FIG. 4

AE Generation Intensity (Amplitude) (dB)

*AE generation intensity=α×current(C-rate)+β*

α: 1.627, β: 29.32
Charge-Discharge Current (C-Rate)
FIG. 5

| Slope (α) value | Intercept (β) value |
|---|---|
| ■ Slope | ♦ Intercept |
| — Linear (slope) | Linear (intercept) |

Number of Times of Cycles Tested so Far to Measured Cell
Relation Between the Number of Times of Cycles in the Past To Cell and Intercept and Slope
FIG. 6

| 101 | AC analyzer |
| 111 | Charge-discharge controller |
| 112 | Charge-discharge power supply |

FIG. 7

| 104 | AE analyzer (charge-discharge controller) |
| 112 | Charge-discharge power supply |

FIG. 8

| 105 | Battery module controller (AE analyzer) |

What is claimed is:

1. An inspection apparatus for a lithium ion secondary battery in which an electrolyte and an electrode group are disposed in a container, the electrode group including a positive electrode, a negative electrode, and a separator, the inspection apparatus comprising:
    a charge-discharge power supply for providing a plurality of charge and discharge currents to the lithium ion secondary battery;
    an AE sensor for detecting an acoustic emission generated in the container when charge current or discharge current is provided between the positive electrode and the negative electrode; and
    an AE analysis device for judging a state of the lithium ion secondary battery based on an amplitude intensity of the acoustic emission detected by the AE sensor;
    wherein the AE analysis device conducts a linear approximation for a value of the charge current or a value of the discharge current and the amplitude intensity of the acoustic emission, and estimates a number of charge-discharge cycles that have been provided to the lithium ion secondary battery.

2. The inspection apparatus of claim 1, wherein
each of the plurality of charge and discharge currents has a different value, and
the AE analysis device judges the state of the lithium ion secondary battery based on the amplitude intensity of the acoustic emission corresponding to each of the plurality of charge currents and discharge currents.

3. The inspection apparatus of claim 1, wherein
the AE analysis device estimates the number of charge-discharge cycles by using a slope and an intercept of the linear approximation.

4. The inspection apparatus of claim 1, wherein
the AE sensor is attached to an outside of the container.

5. An inspection method for a lithium ion secondary battery in which an electrolyte and an electrode group are disposed in a container, the electrode group including a positive electrode, a negative electrode, and a separator, the method comprising:
    detecting an acoustic emission generated in the container when charge current or discharge current is provided between the positive electrode and the negative electrode, and
    judging a state of the lithium ion secondary battery based on an amplitude intensity of the detected acoustic emission,
    wherein during said judging, a linear approximation is conducted for a value of the charge current or a value of the discharge current provided to the lithium ion secondary battery, and the amplitude intensity of the acoustic emission.

6. The inspection method of claim 5, wherein
during said detecting, a plurality of charge currents or discharge currents, each having different values, are provided between the positive electrode and the negative electrode, and
during said judging, the state of the lithium ion secondary battery is judged based on the amplitude intensity of the acoustic emission corresponding to each of the plurality of charge or discharge currents.

7. The inspection method of claim 5, wherein
during said judging, a number of charge-discharge cycles is estimated by using a slope and an intercept of the linear approximation.

8. A secondary battery module having a plurality of lithium ion secondary batteries, each lithium ion secondary battery including an electrolyte and an electrode group disposed in a container, the electrode group including a positive electrode, a negative electrode, and a separator, the secondary battery module comprising:
    a charge-discharge power supply for providing a plurality of charge and discharge currents to the plurality of lithium ion secondary batteries;
    an AE sensor for detecting an acoustic emission generated in the container for each of the plurality of lithium ion secondary batteries when charge current or discharge current is provided between the positive electrode and the negative electrode; and
    an AE analysis device for judging a state of the lithium ion secondary battery based on an amplitude intensity of the acoustic emission detected by the AE sensor;
    wherein the AE analysis device conducts a linear approximation for a value of the charge current or a value of the discharge current and the amplitude intensity of the acoustic emission, and estimates a number of charge-discharge cycles that have been provided to the lithium ion secondary battery.

* * * * *